US006359001B1

(12) United States Patent
Drago

(10) Patent No.: US 6,359,001 B1
(45) Date of Patent: Mar. 19, 2002

(54) USE OF α-METHYL-P-TYROSINE TO INHIBIT MELANIN PRODUCTION IN IRIS MELANOCYTES

(75) Inventor: Filippo Drago, Catania (IT)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/403,524

(22) PCT Filed: Apr. 21, 1998

(86) PCT No.: PCT/EP98/02365

§ 371 Date: Jan. 21, 2000

§ 102(e) Date: Jan. 21, 2000

(87) PCT Pub. No.: WO98/47515

PCT Pub. Date: Oct. 29, 1998

(30) Foreign Application Priority Data

Apr. 22, 1997 (IT) .......................................... MI97A0939

(51) Int. Cl.⁷ ............................................... A01N 37/08
(52) U.S. Cl. ....................... 514/530; 514/567; 514/573; 514/912; 514/913
(58) Field of Search .................................. 514/530, 567, 514/57, 573, 913, 912

(56) References Cited

PUBLICATIONS

Chemical Abstracts 68:86079 (1968). Engelman et al.*
Chemical Abstracts 82:83552 (1974). Lindquist*
Chemical Abstracts: vol. 79, No. 5, Aug. 6, 1973, abstract No. 27296.
Odin, Lanny et al: Invest. Opthalmol. Visual Sci. (1982).
Alm A.: Progress In Retinal And Eye Research, (1998), 17/3 (291–312).

* cited by examiner

*Primary Examiner*—Zohreh Fay
(74) *Attorney, Agent, or Firm*—Birch, Stewart, Kolasch & Birch, LLP

(57) ABSTRACT

The use of agents for blocking the synthesis of tyrosinase to prevent permanent pigmentation of the iris caused by melanin deposit induced by pharmacological treatments or by metabolic imbalance is described.

10 Claims, No Drawings

USE OF α-METHYL-P-TYROSINE TO INHIBIT MELANIN PRODUCTION IN IRIS MELANOCYTES

This application is the national phase under 35 U.S.C. § 371 of PCT International Application No. PCT/EP98/02365 which has an International filing date of Apr. 21, 1998, which designated the United States of America.

The present invention refers to the use of agents for blocking the synthesis of tyrosinase to prevent permanent pigmentation of the iris caused by melanin deposit induced by pharmacological treatments or by metabolic imbalance.

BACKGROUND OF THE INVENTION

Latanoprost (13,14-dihydro-17-phenyl-18,19,20-tri- nor- $PGF_{2\alpha}$ isopropyl ester), a synthetic prostaglandin analogue, (EP-A-0364317) as well as naturally occurring prostaglandins such as $PGF_{2\alpha}$ and $PGE_2$ have been shown to induce increased pigmentation of the monkey iris during chronic treatment (Selén G., Stjernschantz J., Resul B. prostaglandin-induced iridial pigmentation in primates. Surv. Ophthalmol 1997; 41, Suppl. 2: S125–S128). The exact mechanism behind this response to prostaglandin treatment is not known, but increased synthesis of melanin (melanogenesis) must occur for the eye colour to become darker. Also in patients treated with latanoprost (Wistrand P J, Stjernschantz J., Olsson K. The incidence and time-course of latanoprost-induced iridial pigmentation as a function of eye color. Surv. Ophthalmol 1997; 41, Suppl. 2:S129–S138) or with isopropyl unoprostone (13,14-dihydro-15-keto-20-ethyl-$PGF_{2\alpha}$ isopropylester) (Yamamoto T., Kitazawa Y. Iris-color change developed after topical isopropyl unoprostone treatment *J. Glaucoma* 1997; 6: 430–432) a darkening of the iris is sometimes noted during chronic therapy. Particularly patients with heterochromic iris, i.e. blue-brown, gray-brown, green-brown or hazel eye colour seem to be predisposed to this side-effect. Since the side-effect may become cosmetically disturbing, particularly in patients with unilateral glaucoma that are treated only in one eye, and since the side-effect is irreversible, and relatively frequent, it would be advantageous to circumvent it, although it does not appear to pose a health hazard to the patients that develop it.

Melanin, a large naturally occurring polymer is formed from the amino acid tyrosine. In the initial step of melanin formation tyrosine is hydroxylated to L-Dopa which is further oxidized to dopaquinone. The enzyme catalyzing both reactions is called tyrosinase. Dopaquinone is a labile compound that is converted to dopachrome, a black compound which is needed for the formation DHICA (dihydroxyindol-carboxylic acid) oligomers that are needed for the final polymerisation to yield eumelanin (black or brown melanin). Dopaquinone can alternatively react with cysteine which will lead to sulfur containing oligomers and finally pheomelanin (yellowish or reddish melanin). Important to realize is that the rate limiting step in the melanin production is the reaction catalyzed by tyrosinase. Lack of functional tyrosinase e.g. because of a mutation of the tyrosinase gene, always leads to albinism since no pigment can be formed in the body. Interestingly, the same tyrosinase enzyme is also needed in sympathetic neurons and adrenal medulla for the production of noradrenaline, a neurotransmitter, and adrenaline, a hormone, since these compounds are biosynthetized from tyrosine. Thus compounds that block the tyrosinase enzyme will have effect both on melanogenesis and on the function of the sympathetic nervous system.

SUMMARY OF THE INVENTION

It has now been found that inhibitors of the tyrosinase enzyme, particularly, α-methyl-p-tyrosine, inhibit melanin production induced by administration of $PGF_{2\alpha}$, and $PGE_2$ derivatives, such as latanoprost and unoprostone.

Thus, the treatment with said tyrosinase inhibitors prior, during or after administration of prostaglandin derivatives in glaucomatous patients, inhibits melanin production by iris melanocytes avoiding the eye coloring variations in these patients.

DETAILED DESCRIPTION OF THE INVENTION

A classical agent for blocking the synthesis of tyrosine hydroxylase is α-methyl-para-tyrosine, a drug known with the name of metyrosine (J. Am. Chem. Soc. 77, 700, 1958), which is a false substrate for the enzyme. Thus L-Dopa is not formed and consequently neither malanin nor adrenaline/noradrenaline can be formed. The drug has been used in the palliative treatment of pheocromocytoma, a tumour of the adrenal medulla leading to high concentrations of catecholamines in blood and therefore increased blood pressure. Used in concentrations high enough, α-methyl-para-tyrosine can significantly block the biosynthesis of adrenaline/noradrenaline as well as malanin. When used at clinical concentrations for the treatment of pheocromocytoma the catecholamine concentration in the body is markedly reduced (Weiner N., Drugs that inhibit adrenergic nerves and block adrenergic receptors. In Goodman Gilman A., Goodman L S, Rall T W, Murad F., eds; *Goodman and Gilman's the Phar-macological Basis of Therapeutics*, Macmillan, N. Y., 1985, pp 181–214), and in the in vitro experiments of the present inventions the melanin production was significantly reduced. In essence any agent that interfers with the tyrosinase enzyme will have the same beneficial effect resulting in a blockade of the melanin production.

Such agents are e.g. hydroxyquinone and substances that react with copper ions because copper is a necessary cofactor for the tyrosinase enzyme, and various kinds of false substances for the enzyme. Consequently if these agents are given either separately or in a mixture together with latanoprost, isopropyl unoprostone, or any other protaglandin that induces melanogenesis, the pigment formation in the iris can be prevented or at least significantly hindered.

This activity of α-methyl-p-tyrosine has been demonstrated with the following experiments:

MATERIALS AND METHODS

Cell Culture

Uveal melanocytes were isolated and cultured from adult donor eyes. The iris was excised and placed in a dish with the posterior surface upward. The iris pigment epithelium was separated from the stroma after immersion in 0.25% trypsin solution (Gibco, USA) at 37° C. for 2 hour. The remaining iris stroma was placed in a 0.25% trypsin solution at 4° C. for 18 hours, followed by incubation at 37° C. for 1 hour. The isolated cells were collected. The trypsin solution was replaced by collagenase solution (400 U/ml, in F-12 medium, Sigma, USA) and incubated at 37° C. The collagenase solution was replaced, and the cells were collected, centrifuged, resuspended, and plated each hour for 3 hours.

The isolated uveal melanocytes were cultured in Falcon culture dishes (Becton Dickinson, USA) with FIC medium, which consisted of F-12 medium supplemented with 10% fetal bovine serum, 2 mM glutamine (all from Gibco), 10 ng/ml cholera toxin, 0.1 mM isobutylmethylxanthine, 50

μg/ml gentamicin (all from Sigma), and 20 ng/ml basic fibroblast growth factor (Promega, USA). The culture dishes were incubated in a humidified 5% $CO_2$ atmosphere. The medium was changed three times a week. Geneticin (Sigma, USA); a cytotoxic agent, was added (100 μg/ml) for 3 to 7 days when necessary.

The 8 cell strains of uveal melanocytes used in the present study were isolated from donors with different iris color (brown and brown-blue).

Melanin measurement

Cultured uveal melanocytes were detached by trypsin-EDTA solution and counted in a hemocytometer, the cell suspensions were centrifuged, and the pellet was dissolved in 1 N NaOH. Melanin concentration was determined by measurement of optical density at 475 nm and compared with a standard curve obtained using synthetic melanin (Sigma). Melanin content was expressed as ng/cell.

Calculation of melanin production

Melanin production was calculated by determining the melanin content and the cell counts at the beginning and the end of each generation by the following formula:

$$Cp = CtP - C_0/1.3D \ (P-1)$$

where $C_0$ and $C_t$ represent the melanin content per cell at times 0 and time t, respectively; P is the population increase during time t, D is the doubling time of the uveal melanocytes; and Cp is melanin production per cell per day during time t.

Tyrosinase activity

Tyrosinase activity was evaluated in nine cell strains using an adaptation of the Pomerantz method, which is based on the measurement of $^3H_2O$ released by the enzymatic hydroxylation of tyrosine.

Results

Melanin content in iris melanocytes cultured from 5 cell strains of brown irises and 3 cell strain of brown-blue irises appeared to be increased when latanoprost was added at the highest molar concentrations. The same was found for melanin production and tyrosinase activity (Table 1 and 2).

After α-methyl-p-tyrosine was added ($10^{-5}$ M), a significant decrease in melanin content and production and in tyrosinase activity was found with latanoprost $10^{-7}$ to $10^{-5}$ M both in melanocytes cultured from brown irises and brown-blue irises (Table 1 and 2).

These results show that melanin production by iris melanocytes is inhibited by α-methyl-p-tyrosine.

The present invention also concerns pharmaceutical compositions containing a PGF2α or $PGE_2$ derivative with anti-glaucoma activity and a tyrosinase inhibitor as combined preparations for simultaneous, separate or sequential use in the therapy of glaucoma. In particular, the invention concerns pharmaceutical products containing latanoprost as anti-glaucoma agent and α-methyl-p-tyrosine as combined preparations for simultaneous, separate or sequential use in the therapy of glaucoma.

For the considered therapeutic uses, α-methyl-p-tyrosine will be preferably be administered by topical route or by oral route in a daily dose of about 100–500 mg.

Although the present description concerns particularly the inhibition of melanin production induced by latanoprost, α-methyl-p-tyrosine can be used successfully to inhibit the same side effect of pigmentation induced by other pharmacological treatments or metabolic imbalance of different origin.

TABLE 1

5 cells strains (brown)
- growth stage -

| | Melanin content (ng/cell) | |
|---|---|---|
| | no α-methyl-p-tyrosine | α-methyl-p-tyrosine $10^{-5}$ |
| no latanoprost (control) | 0.0138 | 0.0133 |
| latanoprost $10^{-8}$M | 0.0141 | 0.0135 |
| latanoprost $10^{-7}$M | 0.0151 | 0.0136 |
| latanoprost $10^{-6}$M | 0.0161* | 0.0137 |
| latanoprost $10^{-5}$M | 0.0149* | 0.0131 |

*p < 0.01 vs. control

| | Melanin production (ng/cell/day) | |
|---|---|---|
| | no α-methyl-p-tyrosine | α-methyl-p-tyrosine $10^{-5}$ |
| no latanoprost (control) | 0.0031 | 0.0033 |
| latanoprost $10^{-8}$M | 0.0038 | 0.0035 |
| latanoprost $10^{-7}$M | 0.0046* | 0.0039 |
| latanoprost $10^{-6}$M | 0.0036 | 0.0029 |
| latanoprost $10^{-5}$M | 0.0047* | 0.0031 |

*p < 0.01 vs. control

| | Tyrosinase activity (units) | |
|---|---|---|
| | no α-methyl-p-tyrosine | α-methyl-p-tyrosine $10^{-5}$ |
| no latanoprost (control) | 36.7 | 33.6 |
| latanoprost $10^{-8}$M | 36.7 | 35.5 |
| latanoprost $10^{-7}$M | 38.3 | 38.7 |
| latanoprost $10^{-6}$M | 42.5 | 34.6 |
| latanoprost $10^{-5}$M | 63.1* | 31.5 |

*p < 0.01 vs. control

TABLE 2

3 cell strain (brown-blue)
- growth stage -

| | Melanin content (ng/cell) | |
|---|---|---|
| | no α-methyl-p-tyrosine | α-methyl-p-tyrosine $10^{-5}$ |
| no latanoprost (control) | 0.0121 | 0.0122 |
| latanoprost $10^{-8}$M | 0.0127 | 0.0119 |
| latanoprost $10^{-7}$M | 0.0142* | 0.0123 |
| latanoprost $10^{-6}$M | 0.0149* | 0.0125 |
| latanoprost $10^{-5}$M | 0.0151* | 0.0128 |

*p < 0.01 vs. control

| | Melanin production (ng/cell/day) | |
|---|---|---|
| | no α-methyl-p-tyrosine | α-methyl-p-tyrosine $10^{-5}$ |
| no latanoprost (control) | 0.0021 | 0.0023 |
| latanoprost $10^{-8}$M | 0.0038 | 0.0025 |
| latanoprost $10^{-7}$M | 0.0046* | 0.0029 |
| latanoprost $10^{-6}$M | 0.0056* | 0.0029 |
| latanoprost $10^{-5}$M | 0.0067* | 0.0031 |

*p < 0.01 vs. control

| | Tyrosinase activity (units) | |
|---|---|---|
| | no α-methyl-p-tyrosine | α-methyl-p-tyrosine $10^{-5}$ |
| no latanoprost (control) | 32.5 | 32.4 |
| latanoprost $10^{-8}$M | 33.7 | 34.6 |
| latanoprost $10^{-7}$M | 48.1* | 31.7 |

TABLE 2-continued

| | 3 cell strain (brown-blue) - growth stage - | |
|---|---|---|
| latanoprost $10^{-6}$M | 52.5* | 34.6 |
| latanoprost $10^{-5}$M | 62.7* | 39.5 |

*p < 0.01 vs. control

What is claimed is:

1. A pharmaceutical composition containing a $PGF_{2\alpha}$ derivative compound as an anti-glaucoma agent and a tyrosinase inhibitor, the $PGF_{2\alpha}$ derivative compound and the tyrosinase inhibitor are combined with a pharmaceutically acceptable carrier and formulated in preparations for simultaneous, separate or sequential administration to a patient suffering from glaucoma.

2. The pharmaceutical composition according to claim 1, containing latanoprost as the anti-glaucoma agent and $\alpha$-methyl-p-tyrosine as the tyrosinase inhibitor.

3. A method for preventing iris pigmentation as induced by a $PGF_{2\alpha}$ derivative compound or a $PGE_2$ derivative compound in glaucoma treatment, comprising:
   administration on administering an effective amount of a tyrosine inhibitor with either a $PGF_{2\alpha}$ derivative compound or a $PGE_2$ derivative compound,
   wherein the tyrosine inhibitor is administered simultaneously, separately or sequentially with said derivative compounds.

4. The method according to claim 3, wherein the tyrosine inhibitor is $\alpha$-methyl-p-tyrosine.

5. The method according to claim 3, wherein an effective amount of a tyrosine inhibitor with either a $PGF_{2\alpha}$ derivative compound or a $PGE_2$ derivative compound is administered via a topical route.

6. The method according to claim 3, wherein an effective amount of a tyrosine inhibitor with either a $PGF_{2\alpha}$ derivative compound or a $PGE_2$ derivative compound is administered via an oral route.

7. The method according to claim 3, wherein the $PGF_{2\alpha}$ derivative compound is latanoprost.

8. The method according to claim 3, wherein the $PGE_2$ derivative compound is unoprostone.

9. A pharmaceutical composition containing a $PGE_2$ derivative compound as an anti-glaucoma agent and a tyrosinase inhibitor, the $PGE_2$ derivative compound and the tyrosinase inhibitor are combined with a pharmaceutically acceptable carrier and formulated in preparations for simultaneous, separate or sequential administration to a patient suffering from glaucoma.

10. The pharmaceutical composition according to claim 9, containing unoprostone as the anti-glaucoma agent and $\alpha$-methyl-p-tyrosine as the tyrosinase inhibitor.

* * * * *